(12) United States Patent
Valliant et al.

(10) Patent No.: US 11,491,244 B2
(45) Date of Patent: Nov. 8, 2022

(54) LABELED FLUOROCARBON AGENTS FOR POSITRON EMISSION TOMOGRAPHY IMAGING

(71) Applicants: McMaster University, Hamilton (CA); Sunnybrook Research Institute, Toronto (CA)

(72) Inventors: John Valliant, Ancaster (CA); Naomi Matsuura, Toronto (CA)

(73) Assignees: Sunnybrook Research Institute, Toronto (CA); McMaster University, Hamilton (CA)

( * ) Notice: Subject to any disclaimer, the term of this patent is extended or adjusted under 35 U.S.C. 154(b) by 0 days.

(21) Appl. No.: 16/618,145

(22) PCT Filed: Jun. 4, 2018

(86) PCT No.: PCT/CA2018/050667
§ 371 (c)(1),
(2) Date: Nov. 28, 2019

(87) PCT Pub. No.: WO2018/218376
PCT Pub. Date: Dec. 6, 2018

(65) Prior Publication Data
US 2020/0397922 A1     Dec. 24, 2020

Related U.S. Application Data

(60) Provisional application No. 62/514,182, filed on Jun. 2, 2017.

(51) Int. Cl.
*A61B 5/055* (2006.01)
*A61K 49/10* (2006.01)
*C07C 19/08* (2006.01)

(52) U.S. Cl.
CPC .............. *A61K 49/10* (2013.01); *C07C 19/08* (2013.01)

(58) Field of Classification Search
CPC ................................ C07C 19/08; A61K 49/10
See application file for complete search history.

(56) References Cited

U.S. PATENT DOCUMENTS

| 5,496,535 A | 3/1996 | Kirkland | |
| 6,184,426 B1 * | 2/2001 | Belen'Kill | ............ C07C 17/275 |
| | | | 570/172 |
| 2015/0250905 A1 | 9/2015 | Figdor et al. | |

OTHER PUBLICATIONS

Bříza et al. (J. Fluorine Chem. 2008, 129, 235-247).*
Kim et al. (J. Org. Chem. 2008, 73, 957-962).*
Ruth et al. (J. Radioanalyt. Nucl. Chem. 1996, 203, 457-469).*
Martin et al. (Ultrasound Med. Biol. 2012, 38, 1799-1810).*
Mattrey RF. The potential role of perfluorochemicals (PFC's) in diagnostic imaging. Artif Cells Blood Substitutes Biotechnol 1994;22:295-313.
Rockwell S, Dobrucki IT, Kim EY, Marrison ST, Vu VT. Hypoxia and radiation therapy: past history, ongoing research, and future promise. Curr Mol Med 2009;9:442-58.
Riess JG. Oxygen carriers ("blood substitutes")—raison d'etre, chemistry, and some physiology. Chem Rev 2001;101:2797-920.
Hill ML, Gorelikov I, Niroui F, Levitin RB, Mainprize JG, Yaffe MJ, et al. Towards a na-noscale mammographic contrast agent: development of a modular pre-clinical dual op-tical/x-ray agent. Phys Med Biol 2013;58:5215-35.
Mountford PA, Smith WS, Borden MA. Fluorocarbon nanodrops as acoustic tempera-ture probes. Langmuir 2015;31:10656-63.
Li H, Wang P, Wang X, Yin T, Zhou G, Shuai X, et al. Perfluorooctyl bromide traces self-assembled with polymeric nanovesicles for blood pool ultrasound imaging. Bioma-ter Sci 2016;4:979-88.
Giraudeau C, Djemai B, Ghaly MA, Boumezbeur F, Meriaux S, Robert P, et al. High sensitivity 19F MRI of a perfluorooctyl bromide emulsion: application to a dynamic bio-distribution study and oxygen tension mapping in the mouse liver and spleen. NMR Biomed 2012;25:654-60.
Hughes M, Caruthers S, Tran T, Marsh J, Wallace K, Cyrus T, et al. Perfluorocarbon nanoparticles for molecular imaging and targeted therapeutics. Proc IEEE 2008;96:397-415.
Strohm E, Rui M, Gorelikov I, Matsuura N, Kolios M. Vaporization of perfluorocarbon droplets using optical irradiation. Biomed Opt Express 2011;2:1432-42.
Ke H, Wang J, Tong S, Jin Y, Wang S, Qu E, et al. Gold nanoshelled liquid perfluoro-carbon magnetic nanocapsules: a nanotheranostic platform for bimodal ultra-sound/magnetic resonance imaging guided photothermal tumor ablation. Theranostics 2013;4:12-23.
Rapoport N, Gao Z, Kennedy A. Multifunctional nanoparticles for combining ultrasonic tumor imaging and targeted chemotherapy. J Natl Cancer Inst 2007;99:1095-106.
Vu-Quang H, Vinding MS, Nielsen T, Ullisch MG, Nielsen NC, Kjems J. Theranostic tumor targeted nanoparticles combining drug delivery with dual near infrared and 19F magnetic resonance imaging modalities. Nanomedicine 2016;12:1873-84.
Williams R, Wright C, Cherin E, Reznik N, Lee M, Gorelikov I, et al. Characterization of submicron phase-change perfluorocarbon droplets for extravascular ultrasound imag-ing of cancer. Ultrasound Med Biol 2013;39:475-89.
Sheeran PS, Luois S, Dayton PA, Matsunaga TO. Formulation and acoustic studies of a new phase-shift agent for diagnostic and therapeutic ultrasound. Langmuir 2001;27:10412-20.
Gorelikov I, Martin AL, Seo M, Matsuura N. Silica-coated quantum dots for optical eval-uation of perfluorocarbon droplet interactions with cells. Langmuir 2011;27:15024-33.
Jacoby C, Temme S, Mayenfels F, Benoit N, Krafft MP, Schubert R, et al. Probing dif-ferent perfluorocarbons for in vivo inflammation imaging by 19F MRI: image recon-struction, biological half-lives and sensitivity. NMR Biomed 2014;27:261-71.
Tirotta I, Dichiarante V, Pigliacelli C, Cavallo G, Terraneo G, Bombelli FB, et al. 19F magnetic resonance imaging (MRI): from design of materials to clinical applications. Chem Rev 2015;115:1106-29.

(Continued)

*Primary Examiner* — Michael G. Hartley
*Assistant Examiner* — Melissa J Perreira
(74) *Attorney, Agent, or Firm* — Bereskin & Parr LLP/S.E.N.C.R.L., s.r.l.; Michael Fenwick

(57) ABSTRACT

The present application is in the field of imaging reagents. In particular, the present application relates to labelled fluorocarbon imaging reagents, the preparation of the reagents, and their uses for imaging such as PET scanning.

14 Claims, 9 Drawing Sheets

(56) References Cited

OTHER PUBLICATIONS

Kislukhin AA, Xu H, Adams SR, Narsinh KH, Tsien RY, Ahrens ET. Paramagnetic fluorinated nanoemulsions for sensitive cellular fluorine-19 magnetic resonance imag-ing. Nat Mater 2016;15:662-8.
Long DM, Long DC, Mattrey RF, Long, RA, Burgan AR, Herrick WC, et al. An overview of perfluoroctylbromide—application as a synthetic oxygen carrier and imaging agent for X-ray, ultrasound and nuclear magnetic resonance. Biomater Artif Cells Artif Or-gans 1988; 16:411-40.
Fabiilli ML, Piert MR, Koeppe RA, Sherman PS, Quesada CA, Kripfgans OD. Assess-ment of the biodistribution of an [18F]FDG-loaded perfluorocarbon double emulsion using dynamic micro-PET in rats. Contrast Media Mol Imaging 2013;8:366-74.
Willmann JK, Cheng Z, Davis C, Lutz AM, Schipper ML, Nielsen CH, et al. Targeted microbubbles for imaging tumor angiogenesis: assessment of whole-body biodistribu-tion with dynamic micro-PET in mice. Radiology 2008;249:212-9.
Liao AH, Wu SY, Wang HE, Weng CH, Wu MF, Li PC. Evaluation of 18F-labeled tar-geted perfluorocarbon-filled albumin microbubbles as a probe for microUS and mi-croPET in tumor-bearing mice. Ultrasonics 2013;53:320-7.
Matsuura N, Rowlands JA. Towards new functional nanostructures for medical imag-ing. Med Phys 2008;35:4474-87.
Shao H, Jiang L, Meng W-D, Qing F-L. Synthesis and antimicrobial activity of a per-fluoroalkyl-containing quaternary ammonium salt. J Fluor Chem 2003;124:89-91.
Bříza T, Kvíčala J, Paleta O, Čermák J. 32-(Perfluoroalkyl)ethyl triflates, building blocks for the synthesis of bis (polyfluoroalkylated) cyclopentadienes. Synlett 2001;5:685-7.
Bříza T, Kvíčala J, Paleta O, Čermák J. Preparation of bis(polyfluoroalkyl)cyclopentadienes, new highly fluorophilic ligands for fluorous bi-phase catalysis. Tetrahedron 2002;58:3841-6.
Elshani S, Kobzar E, Bartsch RA. Macrocyclic ligands with par-tially fluorinated sidearms: synthesis and metal ion complexation. Tetrahedron 2000;56:3291-301.
Jadhav VH, Jang SH, Jeong H-J, Lim ST, Sohn M-H, Chi DY, et al. Polymer-supported pentaethylene glycol as a facile heterogeneous catalyst for nucleophilic fluorination. Org Let 2010;12:3740-3.
Williams FM, Draffan GH, Dollery CT, Clark JC, Palmer AJ, Vernon P. Use of 18F la-belled fluorocarbon-11 to investigate the fate of inhaled fluorocarbons in man and in the rat. Thorax 1974;29:99-103.
Jennifer L. Bartels, Tolulope A. Aweda, Adam J. Rosenberg, David M. Lunderberg, Graham F. Peaslee, and Suzanne E. Lapi. Radiosynthesis and Biological Distribution of 18 F-Labeled Perfluorinated Alkyl Substances. Environ. Sci. Technol. Lett. 2017, 4, 211-215.
Normandin MD, Yuan H, Wilks MQ, Chen HH, Kinsella JM, Cho H, et al. Heat-induced radiolabeling of nanoparticles for monocyte tracking by PET. Angew Chem Int Ed Engl 2015;54:13002-6.
Reznik N, Seo M, Williams R, Bolewska-Pedyczak E, Lee M, Matsuura N, et al. Optical studies of vaporization and stability of fluorescently labelled perfluorocarbon droplets. Phys Med Biol 2012;57:7205-17.
Seo M, Gorelikov I, Williams R, Matsuura N. Microfluidic assem-bly of monodisperse, nanoparticle-incorporated perfluorocarbon microbubbles for medical imaging and ther-apy. Langmuir 2010;26:13855-60.
Flogel U, Ding Z, Hardung H, Jander S, Reichmann G, Jacoby C, et al. In vivo monitor-ing of inflammation after cardiac and cerebral ischemia by fluorine magnetic reso-nance imaging. Circulation 2008;118:140-48.
Junjie Chen, Hua Pan, Gregory M. Lanza, and Samuel A. Wickline. Perfluorocarbon Nanoparticles for Physiological and Molecular Imaging and Therapy. Adv Chronic Kidney Dis. Nov. 2013; 20(6): 466-478.

* cited by examiner 0-20 min   20-40 min   40-60 min   60-80 min   80-100 min   100-120 min 0-20 min    20-40 min    40-60 min    60-80 min    80-100 min   100-120 min

LABELED FLUOROCARBON AGENTS FOR POSITRON EMISSION TOMOGRAPHY IMAGING

CROSS REFERENCE TO RELATED APPLICATIONS

This is a national stage application of PCT/CA2018/050667, filed Jun. 4, 2018, which claims priority from U.S. Provisional patent application Ser. No. 62/514,182, filed Jun. 2, 2017, all of which are incorporated herein by reference in their entirety.

FIELD

The present application is in the field of imaging reagents. In particular, the present application relates to labelled fluorocarbon imaging reagents, the preparation of the reagents, and their uses for imaging such as PET scanning.

BACKGROUND

Fluorocarbon droplets are biocompatible, multifunctional materials with wide-ranging applications in medicine. Fluorocarbons are strongly lipophobic and hydrophobic molecules that are emulsified into water-soluble, shell-stabilized droplets prior to intravenous injection. Fluorocarbon droplets have a long history of use in patients as contrast media [1], radiosensitizers [2], and as oxygen carriers [3]. More recently, nanoscale FC droplets have been applied as contrast agents for mammography [4], ultrasound sonothermometry [5], tumor capillary imaging [6], $^{19}F$ magnetic resonance imaging [7,8], and as in situ light [9] and ultrasound activated theranostic agents [10-14]. In addition to FC droplets, other fluorocarbon agents include fluorocarbon bubbles.

Typically, the FC type and the shell stabilizer used (e.g., lipids, proteins, or fluorosurfactants) determine the physical properties of the final FC droplets, including size, size distribution, surface charge and stability [15]. These properties will in turn influence how the particular agent distributes, accumulates and clears in vivo [16,17] and whether their time-dependent distribution can detect or treat abnormal physiology associated with disease sites, such as cancer [11,13] or atherosclerosis [8]. Consequently, different FC droplet formulations all require independent verification of their biodistribution to support optimization and translation to the clinic.

Presently, in vivo imaging modalities that detect FCs droplets are limited in their ability to assess quantitatively the whole-body distribution of the droplets at the sensitivities required to measure low, physiologically significant, concentrations. Although techniques for enhancing the sensitivity of magnetic resonance imaging (MRI) using a new generation of $^{19}F$-based FC droplets has been described recently [18], computed tomography and MRI still require relatively high concentrations of contrast agents for imaging [4,8]. Ultrasound and photoacoustic imaging are further limited by their relatively shallow tissue depth penetration and inability to do whole subject imaging. Alternative approaches are needed to support the assessment of novel FC-based imaging and therapeutic constructs in vivo.

Nanoscale FC droplets have been used to create imaging agents and drug delivery vehicles. One of the most effective and convenient means to track and quantify the biodistribution of new agents such as nanoparticles in preclinical models and patients is by positron emission tomography (PET) [19]. PET can accurately determine the biodistribution of radiolabelled FC agents including clearance route, the extent and rate of removal from the blood pool, and their interaction with the mononuclear phagocyte system. Many of these processes occur within the first few hours after injection, which aligns with the half-life of the most commonly used PET isotope, fluorine-18 ($t_{1/2}$=108 min).

Methods to radiolabel FC droplets have been limited. [18F] Fluorodeoxyglucose ([$^{18}F$]FDG) has been incorporated in the inner aqueous phase of micron-scale, FC double emulsion droplets [20], but leakage from the droplets makes it impossible to distinguish between free FDG and the location of the FC droplets. Furthermore, FC double-emulsion droplets are relatively large (micron-scale), and the labelling methodology cannot be easily adapted for nanoscale droplets (~100 to ~400 nm); the size that is of primary interest for molecular imaging and targeted drug delivery applications. Other radiolabelling methods that could be translated to FC droplets include labelling the stabilizing shell with antibodies conjugated to lipids [21] or albumin [22], which have been previously employed to track micron-scale FC bubble agents with PET. However, shell labelling requires different protocols for different shell materials, and the molecules used to stabilize the shell can easily dissociate from unstable fluorocarbon nanodroplets [23].

SUMMARY

Development and characterization of new formulations of FC agents such as FC droplets are hindered because of the lack of simple methods for quantitative and sensitive assessment of whole body tissue distribution and pharmacokinetics of the droplets. In one embodiment, the present disclosure includes a general-purpose method for radiolabeling the inner core of fluorocarbon agents, such as nanoscale perfluorocarbon droplets, with a hydrophobic and lipophobic fluorine-18 compound.

Accordingly in one aspect, the present invention includes a method for producing a fluorine-18 labeled compound having the structure:

Formula I wherein
a is an integer from 1-50;
b is an integer from 2-10.
comprising the steps of:
i) Synthesis of a fluorocarbon tosylate precursor containing an alkyl spacer
ii) Reacting the fluorocarbon tosylate with [$^{18}F$]F$^-$ to produce a [$^{18}F$] labeled fluorocarbon compound In one embodiment, there is included a method of producing a fluorine-18 labeled compound having the structure:

Formula II comprising the steps of:
i) Synthesis of CF$_3$(CF$_2$)$_7$(CH$_2$)$_3$OTs
ii) Reacting CF$_3$(CF$_2$)$_7$(CH$_2$)$_3$OTs with [$^{18}F$]F$^-$ to produce the [$^{18}F$] labeled fluorocarbon compound The present disclosure also includes fluorine-18 labeled compounds having the structure:

Formula I wherein
a is an integer from 1-50;
b is an integer from 2-10.
In one embodiment, the compound of the formula (I) is CF$_3$—(CF$_2$)$_7$—(CH$_2$)$_3$-$^{18}F$.

In another embodiment of the disclosure there is included a method of imaging a subject comprising administering an effective amount of a fluorine-18 labeled imaging reagent of the disclosure to the subject, wherein the imaging is positron emission tomography (PET) scanning. In another embodiment, there is also includes a method for determining the quantitative biodistribution of FC nanodroplets in a subject, comprising administering an effective amount of a fluorine-18 labeled imaging reagent of the disclosure to the subject, and imaging the subject to measure and determine the biodistribution of the FC nanodroplet.

The present disclosure also includes FC nanodroplets comprising a fluorocarbon agent and a fluorine-18 labeled compound of the Formula I.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

Figure 7:
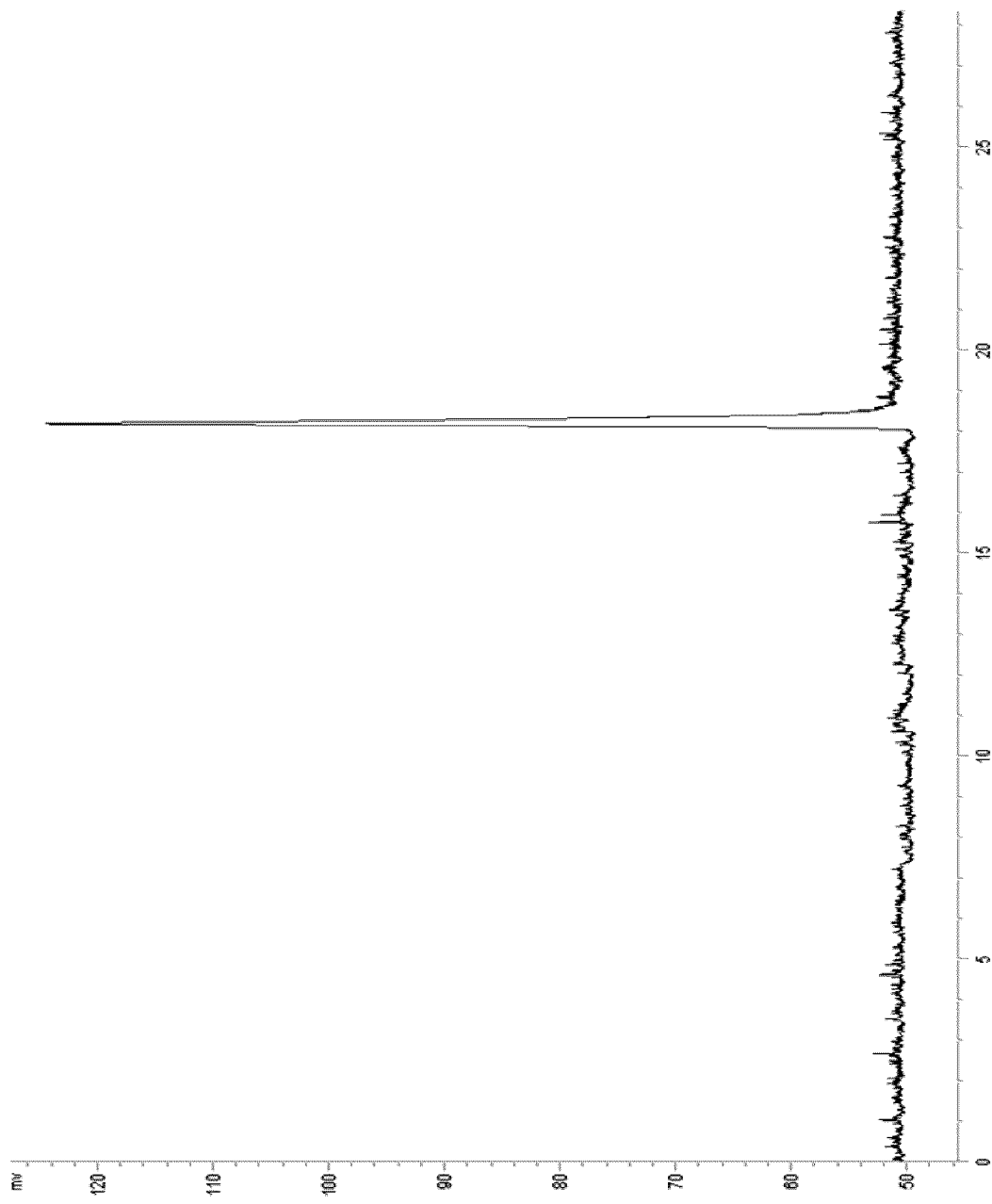

FIG. 7: γ-HPLC chromatogram of a compound of the disclosure.

Figure 8:
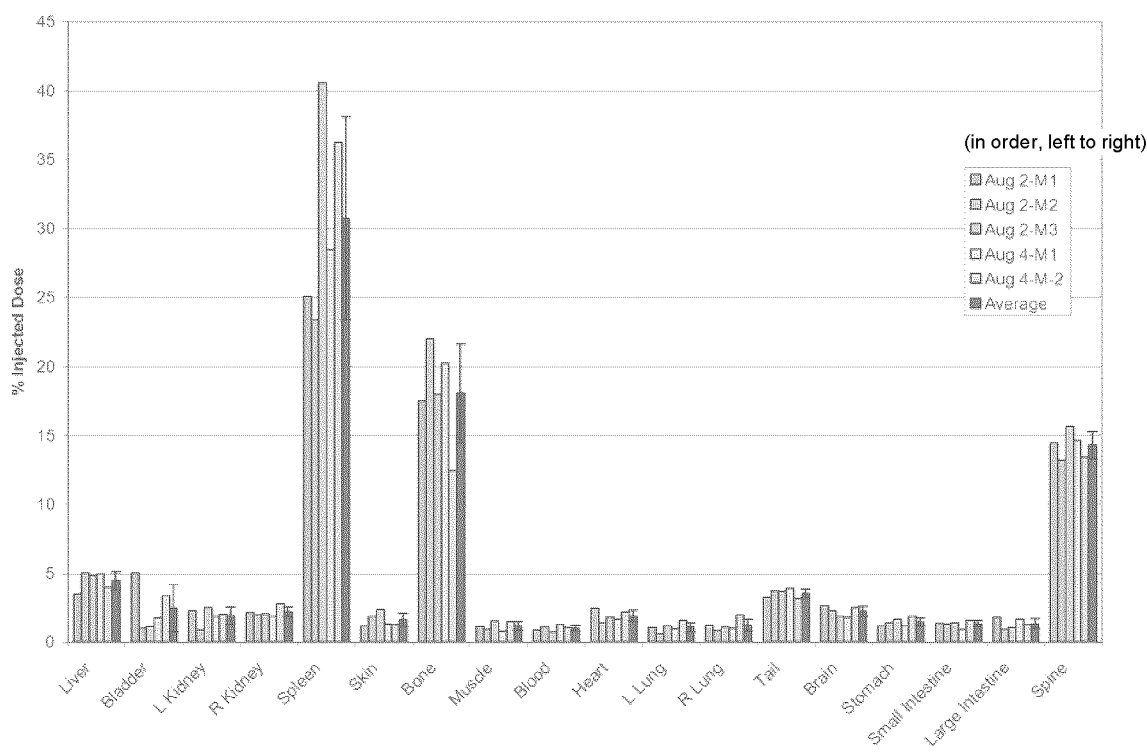

FIG. 8 shows biodistribution data for all mice injected with an imaging reagent of the disclosure.

Figure 9:
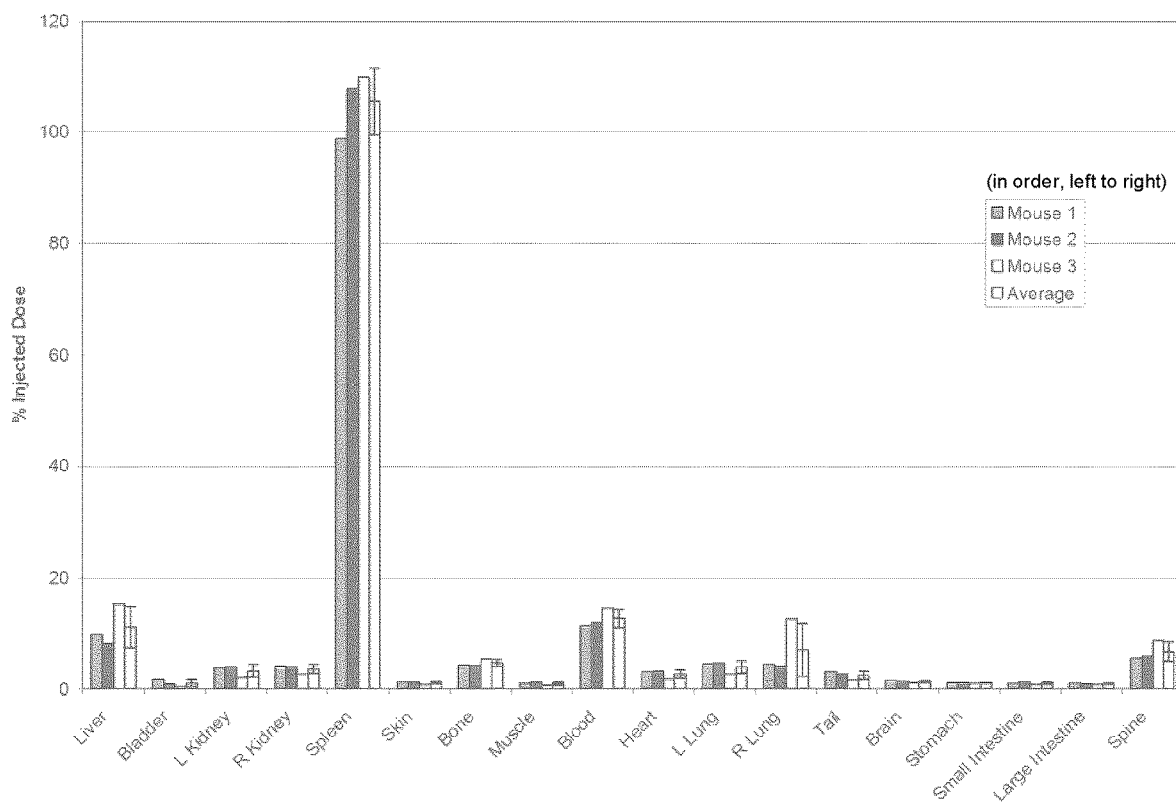

FIG. 9 shows biodistribution data for all mice injected with an imaging reagent of the disclosure (percent injected dose per gram, % ID/g).

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a [imaging reagent, fluorocarbon agent or fluorocarbon droplet]" should be understood to present certain aspects with one substance or two or more additional substances.

In embodiments comprising an "additional" or "second" component, such as an additional or second [imaging reagent, fluorocarbon agent or fluorocarbon droplet], the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

II. Fluorine-18 Labeled Compounds

The present disclosure relates to a fluorocarbon-soluble PET tracer that can be incorporated into the core of nanoscale FC droplets. In one embodiment, the disclosure includes a fluorine-18 labelled molecule that is miscible in any type of FC agent and can be used to perform direct, dynamic and spatial assessment of different nanoscale FC droplet formulations in preclinical models. In one embodiment, the imaging reagent is useful in methods for assessing blood half-life, overall tissue distribution including tissues associated with the mononuclear phagocyte system and in general to facilitate the rapid identification of promising candidate FC agents. Accordingly, the disclosure features an imaging reagent comprised of a fluorocarbon agent containing a fluorine-18 labeled compound. In one embodiment, the imaging reagent is comprised of a microscale fluorocarbon agent containing a fluorine-18 labeled compound. In another embodiment, the imaging reagent is comprised of a sub-microscale fluorocarbon agent containing a fluorine-18 labeled compound. In yet another embodiment, the imaging reagent is comprised of a nanoscale fluorocarbon agent containing a fluorine-18 labeled compound.

Accordingly, in one embodiment, there is included an imaging reagent comprised of a fluorocarbon agent and a fluorine-18 labeled compound. In another embodiment, the fluorocarbon agent is a micron scale agent, or a sub-micron scale agent. In another embodiment, the fluorocarbon agent is a nanoscale scale agent.

In one embodiment, the fluorocarbon agent is a fluorocarbon bubble or a fluorocarbon droplet. In another embodiment, the fluorocarbon agent is a fluorocarbon droplet. In another embodiment, the fluorocarbon agent is a perfluorocarbon agent. In another embodiment, the fluorocarbon agent is perfluoro-crown ether (PFCE), perfluoropolyether (PFPE), perfluorohexane or perfluorooctylbromide. In another embodiment, the fluorocarbon agent is a fluorocarbon particle or polymer, which is labeled with the fluorine-18 labeled compound. In one embodiment, the fluorocarbon agent comprises a shell and an inner core (such as a droplet or bubble), and the fluorine-18 labeled compound is within the shell. In another embodiment, the inner core or phase is solid, liquid or gas, or a combination of any one of the phases. In another embodiment, the fluorine-18 labeled compound is non-covalently associated with the fluorocarbon agents or fluorinated micelles, such as Van der Waals or hydrophobic interactions).

In another embodiment, the imaging reagent is a bubble or droplet which comprises the fluorine-18 labeled compound and a miscible solvent. In another embodiment, the miscible solvent is in the inner core or the shell of the bubble or droplet.

In another embodiment, the fluorine-18 labeled compound is a compound of the formula I $$[^{18}F]CF_3(CF_2)_a(CH_2)_bF \qquad \text{Formula I}$$

wherein
a is an integer from 1-50;
b is an integer from 2-10.

In another embodiment, the compound of Formula I is a compound of the Formula II $$[^{18}F]CF_3(CF_2)_7(CH_2)_3F.$$

In another embodiment, the perfluorocarbon droplet is comprised of fluorosurfactant-stabilized perfluorohexane droplets. In another embodiment, the perfluorocarbon droplet is comprised of lipid-stabilized perfluorooctylbromide droplets.

In another embodiment, the present disclosure includes a compound of the Formula I $$CF_3(CF_2)_a(CH_2)_b{}^{18}F, \qquad \text{Formula I}$$

wherein
a is an integer from 1-50;
b is an integer from 2-10.

In another embodiment, a is an integer from 1 to 25, or from 1 to 10. In another embodiment, a is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, b is an integer from 3 to 10. In another embodiment, b is 2, 3, 4, 5, 6, 7, 8, 9 or 10.

In another embodiment, the compound of the Formula I is $$CF_3(CF_2)_7(CH_2)_3{}^{18}F, \qquad \text{Formula II.}$$

In another embodiment of the disclosure, there is included a method for producing a fluorine-18 labeled compound having the structure:

$$[^{18}F]CF_3(CF_2)_a(CH_2)_bF, \qquad \text{Formula I}$$

wherein,
a is an integer from 1-50;
b is an integer from 2-10,
the method comprising the steps of:
i) Synthesis of a fluorocarbon tosylate precursor containing an alkyl spacer;
ii) Reacting the fluorocarbon tosylate with $[^{18}F]F^-$ to produce the $[^{18}F]$ labeled fluorocarbon compound.

In another embodiment, the disclosure includes a method for producing the fluorine-labeled compound wherein a=7 and b=3, having the structure $$[^{18}F]CF_3(CF_2)_7(CH_2)_3F \qquad \text{Formula II}$$

comprising the steps of:
i) Synthesizing $CF_3(CF_2)_7(CH_2)_3OTs$; and
ii) Reacting $CF_3(CF_2)_7(CH_2)_3OTs$ with $[^{18}F]F-$ to produce the $[^{18}F]$ labeled fluorocarbon compound.

In another embodiment, there is included a method for producing a fluorine-18 labeled compound having the structure:

$$CF_3(CF_2)_a(CH_2)_b{}^{18}F, \qquad \text{Formula I}$$

wherein,
a is an integer from 1-50;
b is an integer from 2-10,
the method comprising the steps of:
i) Synthesis of a fluorocarbon precursor containing an alkyl spacer and a leaving group having the formula:

$$CF_3(CF_2)_a(CH_2)_bX, \text{ wherein X is the leaving group;}$$

ii) Reacting the fluorocarbon precursor with $[^{18}F]F^-$ to produce the $[^{18}F]$ labeled fluorocarbon compound.

In one embodiment, the leaving group is a tosyl group, a mesylate group or a triflate group. In another embodiment, the $[^{18}F]F^-$ is from $Cs^{18}F$ or $TBA^{18}F$.

The present disclosure also includes a method of using the imaging reagents of the disclosure with positron emission tomography scanning for in vivo imaging. In another embodiment, there is included a method for using the fluorine-18 labeled imaging reagents for quantitative biodistribution studies for evaluating FC nanodroplets in vivo. In another embodiment, the imaging reagents are used as multi-modal contrast imaging reagents for imaging using $^{19}F$-MRI and PET simultaneously.

In another embodiment, the present disclosure includes a method for in vivo imaging of the oxygenation of a subject, or the imaging of a tumour (for example, a cancerous tumour), wherein a subject is subsequently treated with an anti-cancer agent after the tumour located and imaged using the imaging reagents of the present disclosure.

In another embodiment, the disclosure includes a method for intracellular labeling and in vivo tracking/trafficking comprising administering an imaging reagent of the disclosure, for example to non-invasively assess the location and persistence of cell-based cancer vaccines and other cell-based therapies.

In another embodiment, the imaging reagents of the disclosure are used to improve cellular therapeutics, drug delivery and understanding disease progression by administering the imaging reagents and tracking their progression.

In another embodiment, the disclosure includes a method for imaging a disease where differential tracking of monocytes results in a diagnosis of a disease.

In one embodiment, the disclosure features an imaging reagent comprised of a fluorocarbon bubble containing a fluorine-18 labeled compound. In another embodiment, the imaging reagent is comprised of a fluorocarbon droplet containing a fluorine-18 labeled compound. In one embodiment, the imaging reagent is comprised of a nanoscale perflorocarbon droplet containing a fluorine-18 labeled compound.

In one embodiment, the imaging reagent is comprised of a fluorocarbon agent, wherein the fluorine-18 labeled compound is:

$[^{18}F]CF_3(CF_2)_a(CH_2)_bF$    Formula I wherein, a is an integer from 1-50 and b is an integer from 2-10.

In another embodiment, the imaging reagent is comprised of a fluorocarbon droplet, wherein the fluorine-18 labeled compound is:

$[^{18}F]CF_3(CF_2)_a(CH_2)_bF$    Formula I wherein, a is an integer from 1-50 and b is an integer from 2-10.

In another embodiment, the imaging reagent is comprised of a nanoscale perfluorocarbon droplet, wherein the fluorine-18 labeled compound is:

$[^{18}F]CF_3(CF_2)_a(CH_2)_bF$    Formula I wherein, a is an integer from 1-50 and b is an integer from 2-10.

In one embodiment, the imaging reagent is comprised of a fluorocarbon agent, wherein the fluorine-18 labeled compound is:

$[^{18}F]CF_3(CF_2)_7(CH_2)_3F$    Formula II

In another embodiment, the imaging reagent is comprised of a fluorocarbon droplet, wherein the fluorine-18 labeled compound is:

$[^{18}F]CF_3(CF_2)_7(CH_2)_3F$    Formula II

In another embodiment, the imaging reagent is comprised of a nanoscale fluorocarbon droplet, wherein the fluorine-18 labeled compound is:

$[^{18}F]CF_3(CF_2)_7(CH_2)_3F$    Formula II

In another embodiment, the imaging reagent is comprised of a nanoscale perfluorocarbon droplet, wherein the fluorine-18 labeled compound is:

$[^{18}F]CF_3(CF_2)_7(CH_2)_3F$    Formula II

In one embodiment, the imaging reagent is comprised of a fluorosurfactant-stabilized perfluorohexane droplet, wherein the fluorine-18 labeled compound is:

$[^{18}F]CF_3(CF_2)_7(CH_2)_3F$    Formula II

In another embodiment, the imaging reagent is comprised of a lipid-stabilized perfluorooctylbromide droplet wherein the fluorine-18 labeled compound is:

$[^{18}F]CF_3(CF_2)_7(CH_2)_3F$    Formula II

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

EXAMPLES

The following non-limiting examples are illustrative of the present application:

Materials and Methods

Materials and Instruments

For nanoscale FC droplet synthesis, perfluorohexane (PFH, $C_6F_{14}$, b.p. 56° C. at 1 atm) and perfluorooctylbromide (PFOB, $C_8F_{17}Br$, b.p. 142° C. at 1 atm) were purchased from SynQuest Laboratories (Alachua, Fla., USA). Zonyl® FSO fluorosurfactant for PFH stabilization was purchased from Sigma-Aldrich (Oakville, ON, Canada). The lipids for PFOB stabilization were 2-dipalmitoyl-sn-glycero-3-phosphocholine (DPPC), 1,2-dihexadecanoyl-sn-glycero-3-phosphate (DPPA), and N-(carbonyl-methoxy-polyethyleneglycol-5000)-1,2-dipalmitoyl-sn-glycero-3-phosphoethanolamine (MPEG-5000-DPPE) were purchased from Avanti Polar Lipids (Alabaster, Ala., USA). All chemicals were used as received unless otherwise indicated. Deionized (DI) water (Millipore Milli-Q grade, 18.2 MΩ) was used in all experiments.

For the preparation of the radiolabelled compound and its precursor, chemicals were purchased from Sigma-Aldrich except NaOH, $MgSO_4$ and dioxane, which were purchased from Caledon Labs (Georgetown, ON, Canada), and FC-72 (b.p 56° C., 1 atm) which was purchased from 3M Science (London, ON, Canada). All chemicals were used as received unless otherwise indicated. No carrier added $[^{18}F]$fluoride was produced by the $^{18}O$ (p,n)$^{18}F$ reaction by bombardment of an isotopically enriched $[^{18}O]H_2O$ target using a Siemens RDS 112 (Siemens CTI, Knoxville, Tenn., USA) or a GE PETTrace 880 cyclotron and obtained as a 1:1 v/v acetonitrile-water solution containing Kryptofix (K-222, 0.02 mmol/mL) and $KHCO_3$ (0.04 mmol/mL). Radioactivity was measured in a dose calibrator (Capintec, Ramsey, N.J., USA), or a Wizard 1470 Automatic Gamma Counter (PerkinElmer). Microwave reactions were performed using a Biotage Initiator instrument (Biotage LLC, Charlotte, N.C., USA). Analytical HPLC was performed using an Agilent 1100 series instrument fitted with an Agilent interface 35900E detector, a Bioscan gamma detector and a C18 Phenomenex Gemini column (5 μm, 4.6×250 mm) or a Waters 1525 series instrument fitted with Waters 2489 UV/Vis detector, a Bioscan gamma detector and a C18 Phenomenex Gemini column (5 μm, 4.6×250 mm). Experiments were performed at a flow rate of 1 mL/min, monitoring at 254 nm and using the following elution protocol: solvent A=$H_2O$ (with 0.4% w/w ammonium formate), solvent B=$CH_3CN$; gradient elution; 40% B; 0-14 min; 100% B; 15-25 min; 40% B; 26-30 min. RadioTLC was performed using pre-coated aluminium plates with an eluent of $CH_3CN$:water (95:5) visualized using Perkin-Elmer Cyclone Plus scanner. Mass spectra were obtained using a Waters Micromass Global Ultima Q-TOF instrument in EI mode.

Example 1—Synthesis of $CF_3(CF_2)_7(CH_2)_3OTs$

The tosylate was synthesized following a literature method with minor modifications [24]. $CF_3(CF_2)_7(CH_2)_3OH$ (499 mg, 1.04 mmol) and p-toluene sulfonyl chloride (238 mg, 1.25 mmol) were dissolved in $CH_2Cl_2$ (5 mL). A 50% w/w aqueous solution of NaOH (2.5 mL) was then added and the reaction mixture heated at 50° C. for 24 h. The organic layer was subsequently extracted (3×) with $H_2O$ (30 mL) and brine (30 mL), dried over anhydrous $MgSO_4$ and filtered. The solvent was removed under vacuum and the product isolated by preparative TLC (10:1 v/v petroleum ether/ethyl acetate) in 52% yield. Analytical HPLC; $R_f$=18.4 min. MS/EI+: m/z for $C_{18}H_{13}F_{17}O_3S$: calcd 632.3319, found 632.0316.

Example 2—Preparation of $[^{18}F]CF_3(CF_2)_7(CH_2)_3F$ $[^{18}F]F^-$ (937 MBq) was dried (6×) using azeotropic distillation of $CH_3CN$ (1.0 mL) by heating in an oil bath at 95° C. under Ar. $CF_3(CF_2)_7(CH_2)_3OTs$ (2.0 mg, 3.16 μmol) in $CH_3CN$ (1.0 mL) was added and heated in an oil bath at 75° C. for 30 min. Following completion of the reaction, $H_2O$ (1.0 mL) was added and the resulting mixture was cooled for 10 min. FC-72 (500 μL) was then added and the layers mixed by extraction in an out of a syringe (4×). The FC-72 layer was removed, and passed through a QMA cation exchange cartridge (Waters, Accell Plus QMA Plus Light Cartridge, 130 mg Sorbent per Cartridge, 37-55 μm Particle Size) and 123 MBq of the product was obtained (RCY 15%±3; n=5) decay corrected radiochemical yield).

Example 3—Stability of $[^{18}F]CF_3(CF_2)_7(CH_2)_3F$ in Water, with and without Sonication $[^{18}F]CF_3(CF_2)_7(CH_2)_3F$ (125 MBq) in FC-72 (2 mL) was separated into 4 equal samples, and water (0.5 mL) was added to each with stirring. At 0.5, 1, 2 and 4 h, the water layer was removed and the amount of activity measured. In addition, $[^{18}F]CF_3(CF_2)_7(CH_2)_3F$ (28 MBq) in FC-72 (130 μL) and DI water (2 mL) was suspended in ice and sonicated using a Branson, Digital S450D Sonifer (Emerson Canada, Markham, ON, Canada) for 10 min at 10% amplitude, using 1 second on-1 second off pulses. The samples were centrifuged and the activity in the aqueous layers were measured using a gamma counter.

Statistical Analysis

Correlation between the biodistribution and imaging results was determined using the Pearson correlation test (p<0.05). Statistical comparisons between groups were performed using one-way analysis of variance with Bonferroni post-test with significance level set at p<0.05. Statistical analyses were performed using Prism 5 software (Graphpad Software, La Jolla, Calif., USA).

The $^{18}$-labelled FC droplets can be used for sensitive and quantitative assessment of the whole-body pharmacokinetics of novel nanoscale FC droplets, which may also be combined with PET-MRI. Accordingly, the present application provides a method of using the multi-modal contrast imaging reagents for imaging using $^{19}$F-MRI and PET simultaneously. This provides the means to combine high-resolution anatomical imaging with the ability to obtain quantitative pharmacokinetic data [35].

Example 4—Preparation of $^{18}$F-Labeled Fluorocarbon-Soluble Molecules

A series of different precursors were used to prepare a $^{18}$-labelled FC. The initial approach employed 2-perfluorooctyl ethyliodide $(CF_3(CF_2)_7(CH_2)_2O$ which is commercially available. To assess feasibility, the iodide was treated with different non-radioactive fluoride sources in a variety of solvents, under different temperatures with and without base, which ultimately failed to produce the desired product. The same was observed at the tracer level, where HPLC showed mostly free fluoride and negligible (<1%) product. The focus shifted to using mesylate, triflate and tosylate precursors, where the latter was advantageous because its purity and consumption (for cold reactions) were easily monitored by HPLC.

The mesylate $CF_3(CF_2)_7(CH_2)_2OMs$, tosylate $CF_3(CF_2)_7(CH_2)_2OTs$, and triflate $CF_3(CF_2)_7(CH_2)_2OTf$ precursors were prepared according to literature procedures [25-27], and characterization data matched with the reported values. The precursors were treated with different fluoride sources under a variety of different solvents, temperatures and bases in a microwave reactor. In most cases, the corresponding alkene was the dominant product according to NMR and MS analysis. However the desired product could be obtained when the mesylate $CF_3(CF_2)_7(CH_2)_2OMs$ was treated with CsF in t-amyl alcohol and the product heated at 140° C. in the microwave reactor for 5 min [28] (Table 3). When reactions were repeated at the tracer level with $[^{18}F]F^-$, yields were less than 10%.

The focus shifted to using precursors with a propyl spacer in an attempt to minimize the influence of the electron withdrawing fluorine groups. The mesylate $CF_3(CF_2)_7(CH_2)_3OMs$ and tosylate $CF_3(CF_2)_7(CH_2)_3OTs$ were prepared and labelled with $[^{18}F]F^-$. The tosylate produced the desired compound (RCY 15%±3; n=5) when the reaction was heated to 75° C. for 30 min. While the overall yield was modest, the product could be easily isolated and separated from impurities by liquid-liquid extraction using FC-72 and water. When the FC-72 solution of the product was extracted with water periodically over 4 h, radioHPLC and radioTLC showed no evidence of free $[^{18}F]F^-$.

Discussion

While $^{18}$-labelled $CCl_3F$ (Freon-11) and $CCl_2F_2$ (Freon-12) have been reported and evaluated in vivo [29], the corresponding radiochemical synthesis of higher molecular weight fluorine rich compounds using $[18]F^-$ has only recently been described once, using fluorine $^{19}F \rightarrow ^{18}F$ exchange [30]. The reason for selecting this fluoride source, as opposed to $[^{18/19}F]_2$, is that $[^{18}F]F^-$ is widely available in large quantities in high specific activity from medical cyclotrons. To ensure efficient encapsulation and retention in vivo, compounds were produced that are not volatile at room temperature and that have high weight percent fluorine. To this end, attempts were made to react commercially available 2-perfluorooctyl ethyliodide with fluoride, which failed to produce the desired product using non-radioactive fluoride or $[^{18}F]F^-$. Conversion of the alcohol (2-perfluorooctyl ethanol) to the corresponding triflate, mesylate or tosylate $(CF_3(CF_2)_7(CH_2)_2OMs$, $CF_3(CF_2)_7(CH_2)_2OTs$, $CF_3(CF_2)_7(CH_2)_2OTf)$ was performed subsequently. Only one condition was found that effectively generated the desired product (CsF in t-amyl alcohol, microwave heating at 140° C. for 5 min) where the product $(CF_3(CF_2)_7(CH_2)_2F)$ showed good solubility in FCs. Unfortunately, the method failed to produce the desired compound at the tracer level.

For these reactions, elimination was favored over substitution. Consequently, a FC with a propyl spacer between the perfluorinated chain and the leaving group was employed. This was designed to minimize the influence of the perfluorinated chain on the basicity of the methylene proton at the β-position relative to the leaving group. Using the tosylate $CF_3(CF_2)_7(CH_2)_3OTs$, we were able to generate $[^{18}F]CF_3(CF_2)_7(CH_2)_3F$ in sufficient yield to produce radiolabelled FCs for use in preclinical studies. [$^{18}$F]CF$_3$(CF$_2$)$_7$(CH$_2$)$_3$F showed no signs of loss of fluoride when left in solution over the timeframe used for the imaging studies.

Figure 6:
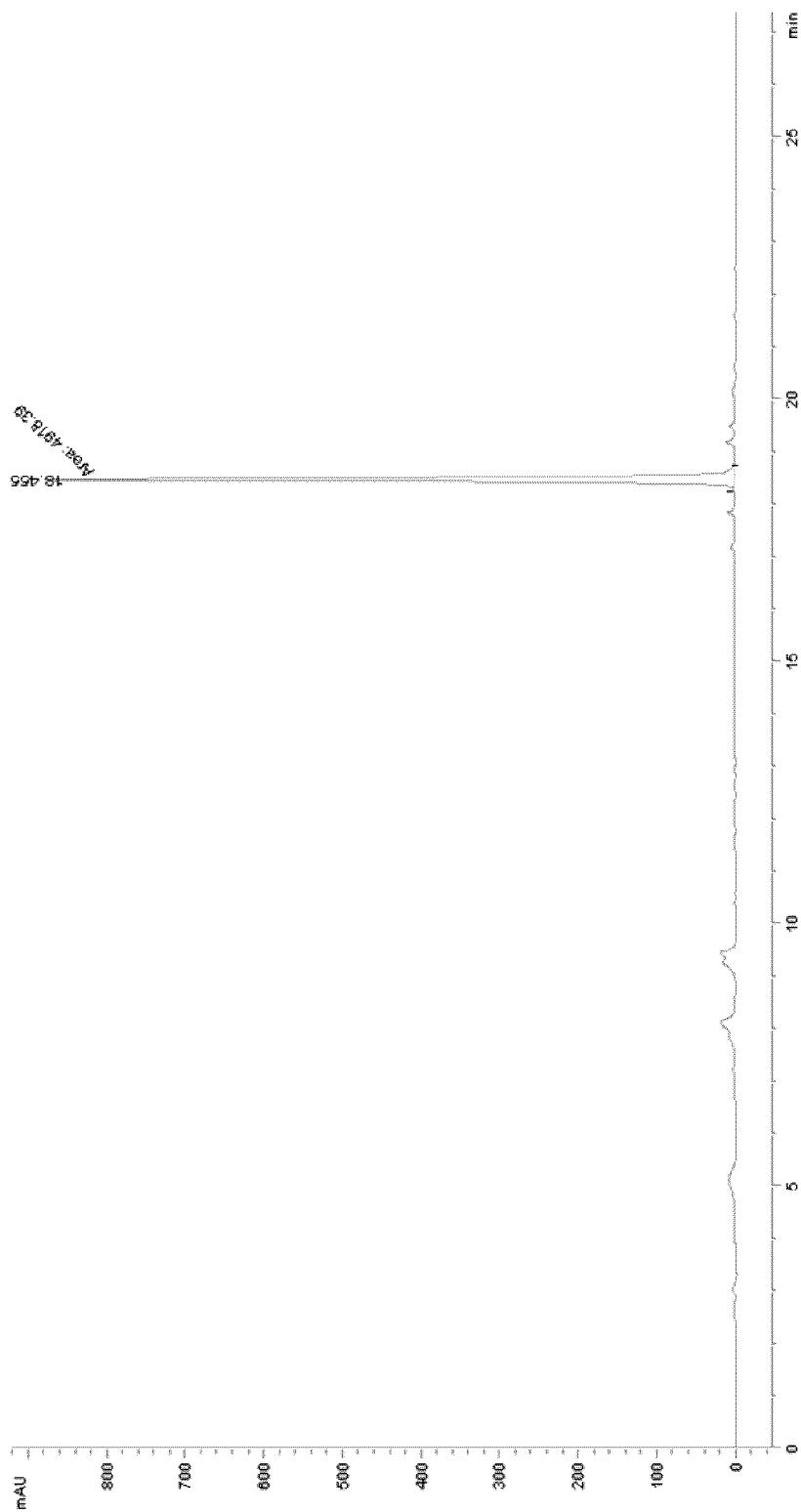
FIG. 6 shows a UV-HPLC chromatogram of a fluorocarbon precursor.

FIG. 6 shows a UV-HPLC chromatogram of CF$_3$(CF$_2$)$_7$(CH$_2$)$_3$OTs. Analytical UV-HPLC chromatogram of CF$_3$(CF$_2$)$_7$(CH$_2$)$_3$OTs.

FIG. 7 shows a γ-HPLC chromatogram of CF$_3$(CF$_2$)$_7$(CH$_2$)$_3$$^{18}$F. γ-HPLC chromatogram of CF$_3$(CF$_2$)$_7$(CH$_2$)$_3$$^{18}$F.

Example 5—Preparation of $^{18}$F-Labelled Fluorocarbon Droplets and Use for In Vivo Imaging The effectiveness of the agent or compound as a tool to study the distribution of FC's in vivo and to label different FC droplets, or other FC agents, creates the ability to distinguish the in vivo behavior of this class of compounds and different FC droplet formulations, which was evaluated using two types of perfluorocarbon nanodroplets as examples: fluorosurfactant-stabilized perfluorohexane (PFH) nanodroplets and lipid-stabilized perfluorooctylbromide (PFOB) nanodroplets. In vivo assessment of the $^{18}$-labelled PFH and PFOB nanodroplets were conducted in normal mice following intravenous injection using small animal PET imaging and gamma counting of tissues and fluids.

[$^{18}$F]CF$_3$(CF$_2$)$_7$(CH$_2$)$_3$F was stable with respect to loss of fluoride in vitro. The labelled FC was successfully integrated into PFH nanodroplets (~175 nm) and PFOB nanodroplets (~260 nm) without altering their mean sizes, size distributions, or surface charges compared to their non-radioactive analogues. No leakage of the radiolabel from the nanodroplets was detected after droplet formation in vitro. PET imaging and biodistribution data for the two droplet types tested showed significantly different tissue uptake and clearance patterns.

To prepare $^{18}$-labelled fluorocarbon droplets, [$^{18}$F]CF$_3$(CF$_2$)$_7$(CH$_2$)$_3$F in FC-72 was added to either PFH or PFOB to a total volume of 65 µL, and then mixed with 2 mL of DI water and 12.5 µL of emulsifier (Zonyl FSO for PFH or a lipid solution for PFOB). Briefly, lipid solutions were prepared by mixing 0.82 mol DPPC, 0.1 mol DPPA, and 0.08 mol MPEG-5000-DPPE, followed by dissolving in chloroform (CHCl$_3$). The chloroform was evaporated under a gentle flow of nitrogen gas, and the resulting lipid dried in a 50° C. vacuum oven overnight to remove residual solvent, followed by at least ten freeze-thaw cycles to form a homogeneous solution. The mixtures were suspended in an ice bath and sonicated with a Branson Digital S450D Sonifer for 10 min. at 10% amplitude, using 1 second on-1 second off pulses. Samples were then centrifuged using an Eppendorf 5430 Centrifuge (Eppendorf Canada, Mississauga, ON, Canada) at 4000 rpm for 20 min. The supernatant was discarded and the precipitate was redispersed in DI water to a droplet volume concentration of 6%. Droplet hydrodynamic diameters and zeta potentials were obtained using a Zetasizer Nano-ZS 3000HS (Malvern Instruments, Worcestershire, UK) dynamic light scattering instrument. The activities of the $^{18}$-labelled droplets pre- and post-synthesis were measured using either a dose calibrator (Capintec CRC-25R well counter, Ramsey, N.J., USA) or a γ-counter (1285 Compugamma CS, LKB Wallac, Turku, Finland) depending on the amount of activity used.

Production and Characterization of $^{18}$F-Labelled Fluorocarbon Droplets

[$^{18}$F]CF$_3$(CF$_2$)$_7$(CH$_2$)F was subsequently solubilized into two different perfluorocarbons, then formed into nanoscale droplets using tip sonication. Lower boiling point PFH nanodroplets stabilized with a non-ionic fluorosurfactant (Zonyl® FSO) [13.15], and higher boiling point PFOB nanodroplets stabilized with a lipid shell [32,33] were selected, as previous reports suggest these nanodroplet formulations would result in different in vivo behaviour. The $^{18}$-labelled perfluorocarbon droplets produced in this study were characterized by mean size, size distribution and surface charge (Table 1). Excellent batch-to-batch reproducibility of mean size, size distribution and charge was found for both types of droplets (PFH, n=4; and PFOB, n=5). No difference in droplet size, size distribution or surface charge was observed compared to non-$^{18}$F-labelled PFH and PFOB droplet controls. After $^{18}$-labelled fluorocarbon droplet formation, the loss of the $^{18}$F[F$^-$] was determined by separating the droplets from the aqueous phase via centrifugation, and subsequent measurements of the activity in the supernatant and pellet. The amount of activity in the aqueous solutions collected was 2.4±0.2% of the total starting activity for both droplet types, which was consistent over a 2 h period following synthesis. This activity was likely due to the presence of ultra-small $^{18}$F-labelled FC droplets/micelles in the supernatant, as no activity was found in the aqueous layer post-sonication without the presence of the stabilizing surfactants.

Animal Studies

C3H/HeJ female mice and CD1 female mice were purchased from Charles River (Kingston, N.Y., USA) and used in PET imaging and biodistribution studies. All animal experiments were conducted under protocols approved by the Animal Care Committee, Sunnybrook Health Sciences Centre, or by the Animal Research Ethics Board at McMaster University, in accordance with Canadian Council on Animal Care (CCAC) guidelines.

Small-Animal PET Studies

To compare the in vivo properties of the 2 different perfluorocarbon droplets using the $^{18}$-labelled fluorocarbon, PET studies were performed using 8-12 week-old C3H/HeJ female mice (n=9) weighing 20-30 g that were anesthetized by inhalation of 2% isoflurane in oxygen for catheterization. Anesthetic maintenance was by additional isoflurane inhalation for PFH droplet experiments and by intramuscular injection of ketamine (15 mg/kg)/xylazine (5 mg/kg) for PFOB droplet experiments. Mice were injected with $^{18}$-labelled PFH droplets (from 1.11 to 2.86 MBq) or $^{18}$F-labelled PFOB droplets (1.58 to 9.62 MBq), via a catheter placed in the animal's tail vein, using total volume of 100 µL at an injection rate of 20 pt/min. After injection, the catheter was removed and the mouse was transferred to the PET system, maintained under anesthesia and kept warmed using a heated bed. Mice were imaged 2 min after injection, and PET scans were performed over a 2 h period using acquisition times of 20 min over 4 bed positions. The PET data were acquired in list mode using a LabPET™-4 scanner equipped with avalanche photodiode detectors (Gamma Medica, Northridge, Calif., USA). The images were then reconstructed using Gamma Medica reconstruction software using MLEM reconstruction with a FOV diameter of 46 mm, a span of 31, and 10 iterations.

The PET imaging signals from various tissues were analyzed through volume-of-interest (VOI) analysis using PMOD software. $^{18}$F with known radioactivity in a water-filled cylinder was used for system calibration. The $^{18}$F-uptake in each tissue was expressed as the percentage of injected dose per gram of tissue (% ID/g).

Quantitative biodistribution studies comparing $^{18}$F-labelled PFH and $^{18}$F-labelled PFOB droplets.

Biodistribution studies in C3H/HeJ mice (n=4 or 5 per group) were performed after completion of the PET studies. Blood was collected via cardiac puncture immediately after the PET scan, and mice were sacrificed at 130±5 min (post initial injection) by cervical dislocation. Organs and tissues (i.e., the liver, bladder, kidneys, spleen, skin, femur, muscle, heart, lungs, tail, brain, small intestine, large intestine, and spine) were collected and weighed, and radioactivity measured in a γ-counter (1285 Compugamma CS). Organ and normal tissue uptake was calculated using the following formula: ((MBq measured in tissue/MBq injected dose)× 100)/g tissue) and expressed as mean±SD % ID/g (% injected dose per g tissue).

PET Imaging and Biodistribution of $^{18}$F-Labelled PFH and $^{18}$F-Labelled PFOB Droplets PET imaging using a small animal PET scanner for 2 h, following tail-vein injection of $^{18}$F-labelled droplets in healthy C3H/HeJ mice, was performed to assess the tissue distribution of the two different formulations. This initial preclinical study utilized healthy mice to remove variability that could result from the use of tumor models (e.g., tumor types, sizes, and locations) that are known to influence the dynamic accumulation of nanoparticles in vivo.

Figure 1:
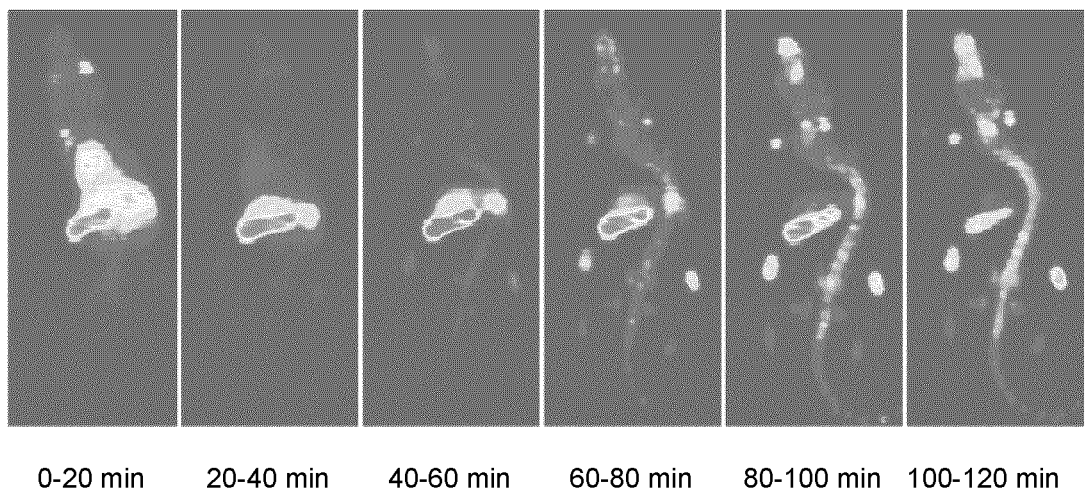
FIG. 1 shows coronal small animal PET images of a C3H/HeJ mouse after injection of an imaging reagent of the disclosure (2.86 MBq) over a 2 h scan time at 20 min intervals.
Figure 2:
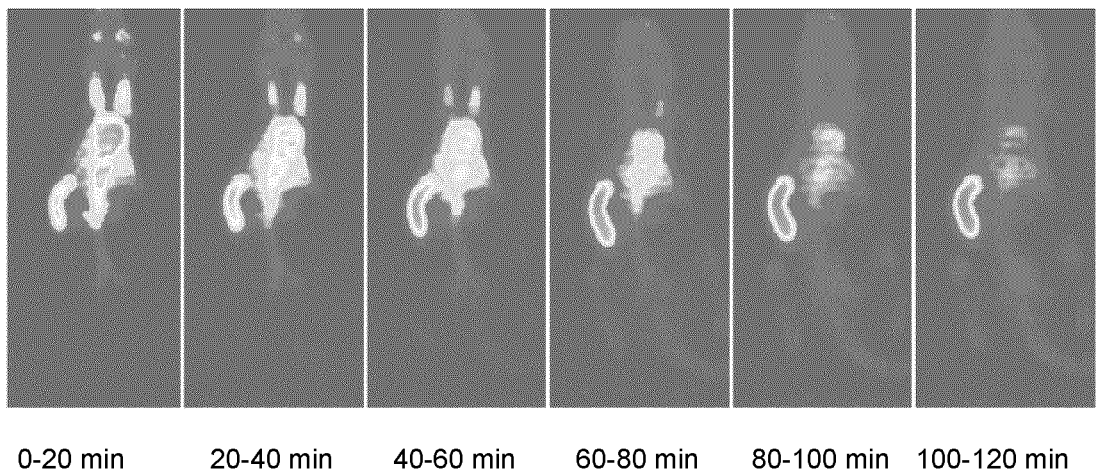
FIG. 2 shows coronal small animal PET images of a C3H/HeJ mouse after injection of an imaging reagent of the disclosure (9.62 MBq) over a 2 h scan time at 20 min intervals.

FIG. 1 and FIG. 2 show typical images of the tissue distribution of the $^{18}$F-labelled PFH and PFOB droplets respectively over a 2 h period. As expected, the distribution differs between the two perfluorocarbon agents. For the $^{18}$F-labelled PFH droplets (FIG. 1), the radioactivity cleared the blood pool within the first 40 min of scanning, and activity appeared to be concentrated within the spleen and liver in the early stages of the scan. This is consistent with similarly emulsified perfluorocarbons used for $^{19}$F MRI, which have been shown to be sequestered by monocytes in the blood [16,34], and subsequently localized to liver, bone and spleen. Interestingly, the labelled material was increasingly taken up in the skeleton (spine and joints) over the time of the scan.

In contrast, the $^{18}$F-labelled PFOB droplets (FIG. 2) had significantly longer residence time in the blood pool, with activity in the heart still observed at the end of the 2 h scan. The radioactivity in the spleen increased gradually over the course of the scan reaching high levels after 1 h. Although some low intensity activity could be observed in the bone, significantly less uptake of the radiotracer was observed in the skeleton in comparison to the $^{18}$F-labelled PFH droplets.

Figure 3:
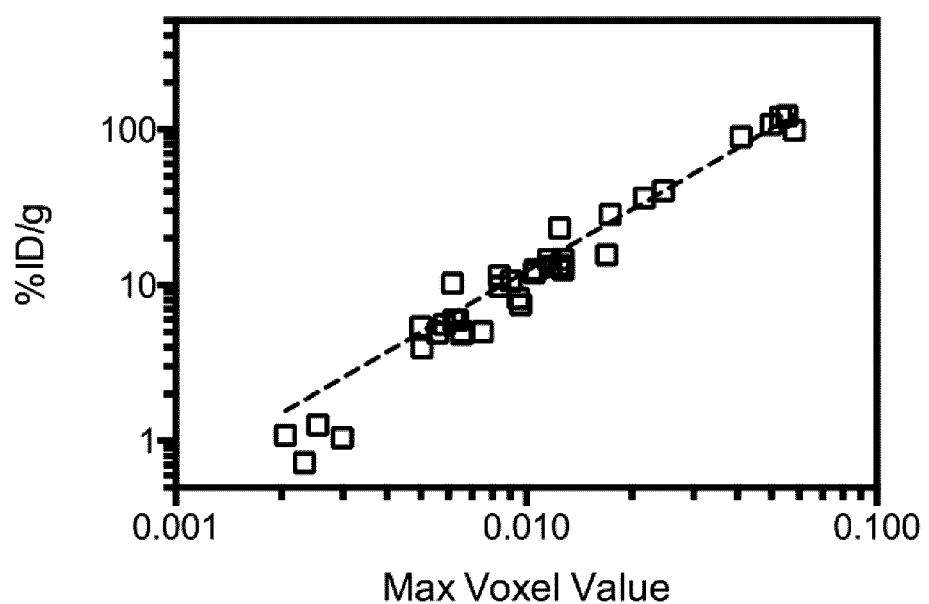
FIG. 3 shows the correlation between the decay-corrected, % ID/g determined by gamma counting of tissues and fluids (y-axis) and the maximum voxel value from VOIs of PET images of the same tissue at the conclusion of the 2 hour scan (x-axis).

After PET scanning, the mice were sacrificed and the radioactivity in the excised tissues measured ex vivo (Table 2) to measure the uptake in various tissues and fluids. A strong correlation between VOI analysis (maximum voxel value) of the small-animal PET images was obtained at 2 h (FIGS. 1 and 2) and the corresponding organ and tissue uptake of radioactivity (% ID/g) measured ex vivo in biodistribution studies (FIG. 3, $R^2$=0.97, p<0.0001; The best fit is represented by the dashed line: % ID/g=(Max Voxel Value)$^m$×10$^b$, where m=[1.31±0.06] and b=[3.71±0.08] ($R^2$=0.97, P<0.0001) was found. The imaging and the ex vivo measurements both showed significantly more radioactivity was found in the bone for the mice injected with the $^{18}$F-labelled PFH droplets (16.2% ID/g) compared to mice injected with $^{18}$F-labelled PFOB droplets (5.7% ID/g). In addition, significantly more radioactivity was found in the spleen (108% ID/g) and in the blood (9.8% ID/g) for mice injected with the $^{18}$F-labelled PFOB compared to the $^{18}$F-labelled PFH droplets (32 and 1.0% ID/g, respectively).

Figure 4:
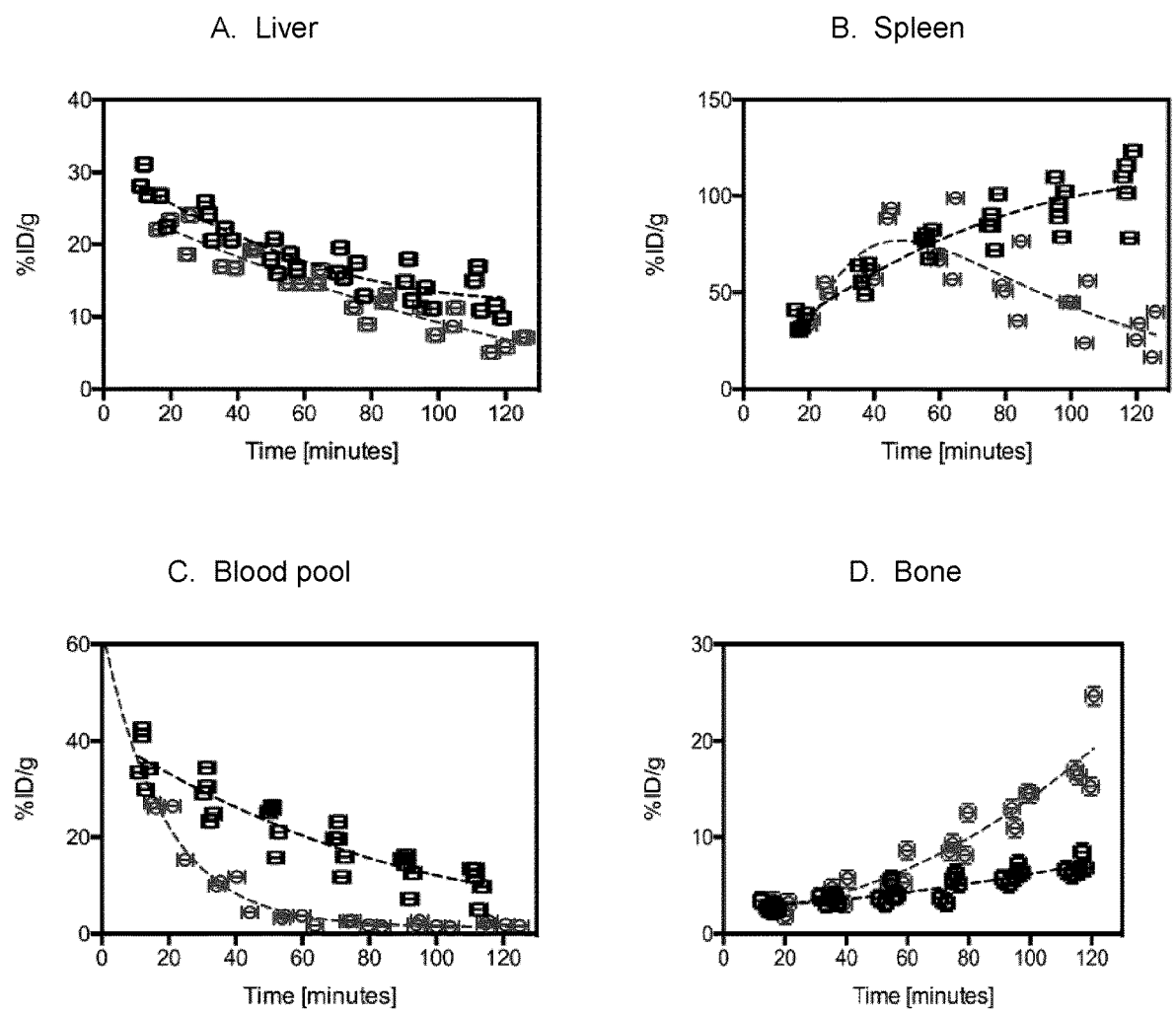
FIG. 4 shows the accumulation of $^{18}F$ in the (a) liver, (b) spleen, (c) blood pool, and (d) bone up to 130±5 min post-injection, as calculated from the PET imaging VOI data, using the best fit correlation (FIG. 3).

The % ID/g calculated from PET imaging as a function of time post-injection was determined for the liver, spleen, blood pool and bone for both $^{18}$-labelled droplets (FIG. 4; Mice (n=4) received $^{18}$-labelled PFH droplets (red circles), or (n=5) mice received $^{18}$-labelled PFOB droplets (black squares). Data indicate the calculated % injected dose per g of tissue (% ID/g)). The liver, spleen, blood pool and bone were selected because they showed the highest uptake in the biodistribution study. For each agent, the dynamic accumulation and clearance followed similar trends among all mice within the group. The liver accumulation was similar for both droplets, continually decreasing over the length of the 2 h scan. However, for the two different droplet types, the accumulation and clearance differed substantially in other organs and blood. The $^{18}$-labelled PFH droplets cleared faster from the spleen (with radioactivity peaking at ~45 to 65 min post-injection), the blood pool (by ~40 min post-injection), and continually accumulated in the bone over the length of the scan. In contrast, $^{18}$F-labelled PFOB droplets demonstrated a continuous increase in uptake by the spleen, slower clearance from the blood pool, and significantly less uptake in the bone over the 2 h.

To ensure that the localization to bone was due to $^{18}$-labelled PFH droplets and not due to the presence of free $^{18}$F[F$^-$], which is known to localize to the skeleton, the [$^{18}$F]CF$_3$(CF$_2$)$_7$(CH$_2$)$_3$F was passed through a cation exchange cartridge prior to the preparation of the perfluorocarbon droplets. This procedure is used widely to trap any residual $^{18}$F[F$^-$] after production on a cyclotron. Following elution of [$^{18}$F]CF$_3$(CF$_2$)$_7$(CH$_2$)$_3$F there was negligible activity remaining on the cartridge. In contrast, a control experiment run in parallel with free $^{18}$F[F$^-$] resulted in retention of all the activity on the resin. In addition, to ensure the observed uptake in bone was not mouse strain dependent, $^{18}$-labelled PFH droplets were prepared and evaluated in CD1 mice using PET. PET images (FIG. 5) were consistent with those shown in FIG. 1 with uptake evident in the spleen, skeleton (notably the knees), and lymph nodes (the white arrows indicate lymph nodes and * indicates uptake in the knee joint. Uptake in the spine and spleen is also evident).

Discussion

In Vitro and In Vivo Evaluation of $^{18}$F-Labelled Perfluorocarbon Droplets

Two different $^{18}$F-labelled perfluorocarbon nanoscale droplets, fluorosurfactant-stabilized PFH and lipid-stabilized PFOB droplets, were selected to evaluate the proposed strategy because their different formulations are expected to result in unique in vivo biodistribution profiles. Both $^{18}$-labeled droplets were produced with consistent sizes and surface charges and with minimal batch-to-batch variability. The consistency of the preparation of each droplet agent is also reflected by the uniformity of the biodistribution data derived from multiple mice tested with each of the $^{18}$-labelled perfluorocarbon droplets (Table 2).

The in vivo studies demonstrated that the $^{18}$F-labeling method can successfully differentiate the in vivo biodistribution of the two different perfluorocarbon microdroplets selected here. The observed biodistribution data for the droplets was consistent with prior reports of the fate of emulsified PFCs in vivo [3,34]. In particular, significant uptake in the liver, spleen, lymph nodes and skeletal system were observed, with the less stable, lower boiling point, and more lipophobic PFH droplets. As expected, the lipid-stabilized, higher boiling point PFOB droplets with increased in vivo stability had a longer blood half-life than PFH droplets. However, the route of clearance of $^{18}$F-labelled PFH droplets was expected to be via exhalation in the lungs, which was not observed over the 2 hour observation period. The results also showed that the smaller PFH droplets were cleared more rapidly from the spleen relative to the larger PFOB droplets.

Figure 5:
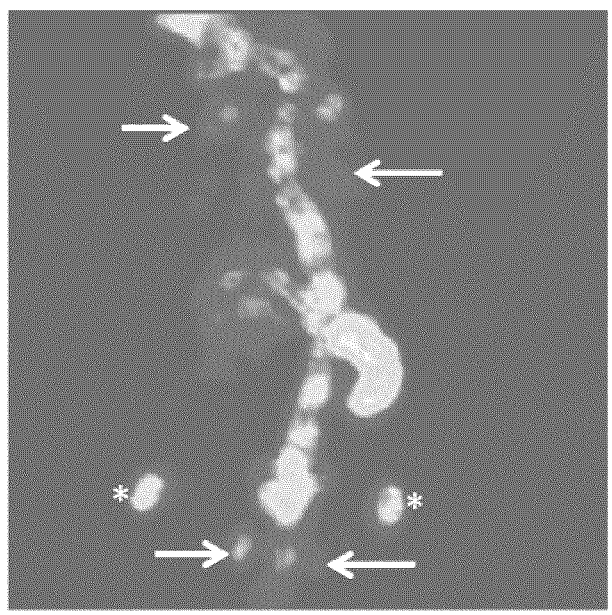
FIG. 5 shows a PET scan of an imaging reagent of the disclosure in a CD1 mouse at 2 h post injection. The white arrows indicate lymph nodes and * indicates uptake in the knee joint.

The $^{18}$F-labelled PFH droplets, when imaged at 2 h, showed greater clearance from the liver and significant uptake in the spine and knees compared to the $^{18}$F-labelled PFOB droplets. In addition, labeling of lymph nodes was clearly evident (FIGS. 1 and 5). This is likely the result of uptake of the droplets by monocytes and subsequent trafficking to lymph nodes, which has been observed to varying degrees with different FC droplet formulations [16,34]. Accordingly, the present invention includes a method of using the imaging agents for in vivo interactions with the mononuclear phagocyte systems.

FIG. 8 shows the biodistribution data for all mice injected with $^{18}$F—PFH droplets. Biodistribution data (percent injected dose per gram, % ID/g) for all mice injected with $^{18}$F—PFH droplets.

FIG. 9 shows the biodistribution data for all mice injected with $^{18}$F—PFOB droplets. Biodistribution data (percent injected dose per gram, % ID/g) for all mice injected with $^{18}$F—PFOB droplets.

TABLE 1

Properties of perfluorocarbon and $^{18}$F-labelled perfluorocarbon droplets

| | Perfluorocarbon | | | $^{18}$F-labelled Perfluorocarbon Droplet | | | |
| --- | --- | --- | --- | --- | --- | --- | --- |
| PFC Type | Boiling point (1 atm) | Density (g/cm$^3$) 25° C. | Water Solubility 25° C. | Stabilizer | Mean Size (nm) | PDI* | Zeta-potential (mV) |
| PFH ($C_6F_{14}$) | 56° C. | 1.71 | Insoluble (<25 ppm) | Zonyl FSO$^†$ | 175 | 0.115 | −0.5 |
| PFOB ($C_8F_{17}Br$) | 142° C. | 1.93 | Insoluble | Lipids | 260 | 0.151 | −12.0 |

*PDI, polydispersity index
$^†$FSO fluorosurfactant

TABLE 2

Biodistribution of $^{18}$F-PFH and $^{18}$F-PFOB droplets following PET imaging study.

| | % ID/g$^†$ ± SD | |
| --- | --- | --- |
| Tissue | $^{18}$F-PFH droplets | $^{18}$F-PFOB droplets |
| Liver | 4.69 ± 0.48 | 11.19 ± 2.49 |
| Kidneys | 2.00 ± 0.55 | 3.14 ± 1.16 |
| Spleen | 32.16 ± 7.70 | 107.80 ± 13.93 |
| Skin | 1.71 ± 0.52 | 1.48 ± 0.38 |
| Bone | 16.19 ± 3.51 | 5.73 ± 1.77 |
| Muscle | 1.17 ± 0.39 | 1.08 ± 0.20 |
| Blood | 1.03 ± 0.23 | 9.81 ± 3.18 |
| Heart | 1.75 ± 0.33 | 2.56 ± 0.65 |
| Lungs | 1.14 ± 0.42 | 4.21 ± 1.29 |
| Brain | 2.11 ± 0.32 | 1.33 ± 0.27 |
| Stomach | 1.53 ± 0.31 | 1.10 ± 0.22 |
| Intestines | 1.26 ± 0.28 | 1.09 ± 0.19 |

$^†$% ID/g, percent injected dose per gram, 2 h post injection.

TABLE 3

Conditions investigated for cold fluorination reactions

| Fluoride Source (eq.) | Starting Material | Base | T(° C.) | Time (h) | Solvent | Result |
| --- | --- | --- | --- | --- | --- | --- |
| TBAF (5) | $CF_3(CF_2)_7(CH_2)_2$OTs | — | 70 | 4 | THF | NR |
| TBAF (5) | $CF_3(CF_2)_7(CH_2)_2$OTs | — | rt | 24 | THF | NR |
| TBAF (2) | $CF_3(CF_2)_7(CH_2)_2$OTs | — | 70 | 1 | t-amyl alcohol | NR |
| NaF (1) | $CF_3(CF_2)_7(CH_2)_2$OTs | KHCO$_3$ | 80 | 0.16 | PFH/MeCN | NR |
| NaF (2) | $CF_3(CF_2)_7(CH_2)_2$OTf | KHCO$_3$ | 60 | 0.16 | PFH/MeCN | NR |
| CsF(3) | $CF_3(CF_2)_7(CH_2)_2$OTs | — | 150 | 0.08 | t-amyl alcohol | NR |
| CsF(3) | $CF_3(CF_2)_7(CH_2)_2$OMs | — | 140 | 0.08 | t-amyl alcohol | 21% |
| CsF(3) | $CF_3(CF_2)_7(CH_2)_2$OTf | — | 140 | 0.08 | t-amyl alcohol | NR |
| TBAF (2) | $CF_3(CF_2)_7(CH_2)_2$OTf | — | 70 | 1 | MeCN | NR |

FULL CITATIONS FOR DOCUMENTS REFERRED TO IN THE APPLICATION

[1] Mattrey R F. The potential role of perfluorochemicals (PFC's) in diagnostic imaging. Artif Cells Blood Substitutes Biotechnol 1994; 22:295-313.

[2] Rockwell S, Dobrucki I T, Kim E Y, Marrison S T, Vu V T. Hypoxia and radiation therapy: past history, ongoing research, and future promise. Curr Mol Med 2009; 9:442-58.

[3] Riess J G. Oxygen carriers ("blood substitutes")—raison d'etre, chemistry, and some physiology. Chem Rev 2001; 101:2797-920.

[4] Hill M L, Gorelikov I, Niroui F, Levitin R B, Mainprize J G, Yaffe M J, et al. Towards a nanoscale mammographic contrast agent: development of a modular pre-clinical dual optical/x-ray agent. Phys Med Biol 2013; 58:5215-35.

[5] Mountford P A, Smith W S, Borden M A. Fluorocarbon nanodrops as acoustic temperature probes. Langmuir 2015; 31:10656-63.

[6] Li H, Wang P, Wang X, Yin T, Zhou G, Shuai X, et al. Perfluorooctyl bromide traces self-assembled with polymeric nanovesicles for blood pool ultrasound imaging. Biomater Sci 2016; 4:979-88.

[7] Giraudeau C, Djemai B, Ghaly M A, Boumezbeur F, Meriaux S, Robert P, et al. High sensitivity $^{19}$F MRI of a perfluorooctyl bromide emulsion: application to a dynamic biodistribution study and oxygen tension mapping in the mouse liver and spleen. NMR Biomed 2012; 25:654-60.

[8] Hughes M, Caruthers S, Tran T, Marsh J, Wallace K, Cyrus T, et al. Perfluorocarbon nanoparticles for molecular imaging and targeted therapeutics. Proc IEEE 2008; 96:397-415.

[9] Strohm E, Rui M, Gorelikov I, Matsuura N, Kolios M. Vaporization of perfluorocarbon droplets using optical irradiation. Biomed Opt Express 2011; 2:1432-42.

[10] Ke H, Wang J, Tong S, Jin Y, Wang S, Qu E, et al. Gold nanoshelled liquid perfluorocarbon magnetic nanocapsules: a nanotheranostic platform for bimodal ultrasound/ magnetic resonance imaging guided photothermal tumor ablation. Theranostics 2013; 4:12-23.

[11] Rapoport N, Gao Z, Kennedy A. Multifunctional nanoparticles for combining ultrasonic tumor imaging and targeted chemotherapy. J Natl Cancer Inst 2007; 99:1095-106.

[12] Vu-Quang H, Vinding M S, Nielsen T, Ullisch M G, Nielsen N C, Kjems J. Theranostic tumor targeted nanoparticles combining drug delivery with dual near infrared and $^{19}$F magnetic resonance imaging modalities. Nanomedicine 2016; 12:1873-84.

[13] Williams R, Wright C, Cherin E, Reznik N, Lee M, Gorelikov I, et al. Characterization of submicron phase-change perfluorocarbon droplets for extravascular ultrasound imaging of cancer. Ultrasound Med Biol 2013; 39:475-89.

[14] Sheeran P S, Luois S, Dayton P A, Matsunaga T O. Formulation and acoustic studies of a new phase-shift agent for diagnostic and therapeutic ultrasound. Langmuir 2001; 27:10412-20.

[15] Gorelikov I, Martin A L, Seo M, Matsuura N. Silica-coated quantum dots for optical evaluation of perfluorocarbon droplet interactions with cells. Langmuir 2011; 27:15024-33.

[16] Jacoby C, Temme S, Mayenfels F, Benoit N, Krafft M P, Schubert R, et al. Probing different perfluorocarbons for in vivo inflammation imaging by $^{19}$F MRI: image reconstruction, biological half-lives and sensitivity. NMR Biomed 2014; 27:261-71.

[17] Tirotta I, Dichiarante V, Pigliacelli C, Cavallo G, Terraneo G, Bombelli F B, et al. $^{19}$F magnetic resonance imaging (MRI): from design of materials to clinical applications. Chem Rev 2015; 115:1106-29.

[18] Kislukhin A A, Xu H, Adams S R, Narsinh K H, Tsien R Y, Ahrens E T. Paramagnetic fluorinated nanoemulsions for sensitive cellular fluorine-19 magnetic resonance imaging. Nat Mater 2016; 15:662-8.

[19] Jin M, Hao G, Sun X, and Chen W. Nanoparticle-based positron emission tomography and single photon emission computed tomography imaging of cancer. Rev. Nanosci. Nanotechnol. 2012; 1:3-21.

[20] Fabiilli M L, Piert M R, Koeppe R A, Sherman P S, Quesada C A, Kripfgans O D. Assessment of the biodistribution of an [$^{18}$F]FDG-loaded perfluorocarbon double emulsion using dynamic micro-PET in rats. Contrast Media Mol Imaging 2013; 8:366-74.

[21] Willmann J K, Cheng Z, Davis C, Lutz A M, Schipper M L, Nielsen C H, et al. Targeted microbubbles for imaging tumor angiogenesis: assessment of whole-body biodistribution with dynamic micro-PET in mice. Radiology 2008; 249:212-9.

[22] Liao A H, Wu S Y, Wang H E, Weng C H, Wu M F, Li P C. Evaluation of $^{18}$-labeled targeted perfluorocarbon-filled albumin microbubbles as a probe for microUS and microPET in tumor-bearing mice. Ultrasonics 2013; 53:320-7.

[23] Matsuura N, Rowlands J A. Towards new functional nanostructures for medical imaging. Med Phys 2008; 35:4474-87.

[24] Shao H, Jiang L, Meng W-D, Qing F-L. Synthesis and antimicrobial activity of a perfluoroalkyl-containing quaternary ammonium salt. J Fluor Chem 2003; 124:89-91.

[25] Břiza T, Kvíčala J, Paleta O, Čermák J. 32-(Perfluoroalkyl)ethyl triflates, building blocks for the synthesis of bis(polyfluoroalkylated) cyclopentadienes. Synlett 2001; 5:685-7.

[26] Břiza T, Kvíčala J, Paleta O, Čermák J. Preparation of bis(polyfluoroalkyl)cyclopentadienes, new highly fluorophilic ligands for fluorous biphase catalysis. Tetrahedron 2002; 58:3841-6.

[27] Elshani S, Kobzar E, Bartsch R A. Macrocyclic ligands with partially fluorinated sidearms: synthesis and metal ion complexation. Tetrahedron 2000; 56:3291-301.

[28] Jadhav V H, Jang S H, Jeong H-J, Lim S T, Sohn M-H, Chi D Y, et al. Polymer-supported pentaethylene glycol as a facile heterogeneous catalyst for nucleophilic fluorination. Org Let 2010; 12:3740-3.

[29] Williams F M, Draffan G H, Dollery C T, Clark J C, Palmer A J, Vernon P. Use of 18F labelled fluorocarbon-11 to investigate the fate of inhaled fluorocarbons in man and in the rat. Thorax 1974; 29:99-103.

[30] Burkemper J L, Aweda T A, Rosenberg A J, Lunderberg D M, Peaslee G F, Lapi S E, Radiosynthesis and Biological Distribution of $^{18}$-Labeled Perfluorinated Alkyl Substances. Environ Sci Technol Lett 2017; DOI 10.1021/acs.estlett.7b00042

[31] Normandin M D, Yuan H, Wilks M Q, Chen H H, Kinsella J M, Cho H, et al. Heat-induced radiolabeling of nanoparticles for monocyte tracking by PET. Angew Chem Int Ed Engl! 2015; 54:13002-6.

[32] Reznik N, Seo M, Williams R, Bolewska-Pedyczak E, Lee M, Matsuura N, et al. Optical studies of vaporization and stability of fluorescently labelled perfluorocarbon droplets. Phys Med Biol 2012; 57:7205-17.

[33] Seo M, Gorelikov I, Williams R, Matsuura N. Microfluidic assembly of monodisperse, nanoparticle-incorporated perfluorocarbon microbubbles for medical imaging and therapy. Langmuir 2010; 26:13855-60.

[34] Flogel U, Ding Z, Hardung H, Jander S, Reichmann G, Jacoby C, et al. In vivo monitoring of inflammation after cardiac and cerebral ischemia by fluorine magnetic resonance imaging. Circulation 2008; 118:140-48.

[35] Long D M, Long D C, Mattrey R F, Long, RA, Burgan A R, Herrick W C, et al. An overview of perfluoroctylbromide—application as a synthetic oxygen carrier and imaging agent for X-ray, ultrasound and nuclear magnetic resonance. Biomater Artif Cells Artif Organs 1988; 16:411-40.

The invention claimed is:

1. An imaging reagent comprised of a fluorocarbon agent and a compound of the Formula I,

Formula I wherein a is an integer from 1 to 50;

b is an integer from 2 to 10, and wherein the fluorocarbon agent is a micron scale agent.

2. The imaging reagent of claim 1, wherein the fluorocarbon agent is a sub-micron scale agent.

3. The imaging reagent of claim 1, wherein the fluorocarbon agent is a nanoscale agent.

4. The imaging reagent of claim 1, wherein the fluorocarbon agent is a fluorocarbon bubble.

5. The imaging reagent of claim 1, wherein the fluorocarbon agent is a fluorocarbon droplet.

6. The imaging reagent of claim 1, wherein the fluorocarbon agent is a perfluorocarbon agent.

7. The imaging reagent of claim 1, wherein the fluorocarbon agent is a perfluorocarbon droplet.

8. The imaging reagent of claim 7, wherein the perfluorocarbon droplet comprises fluorosurfactant-stabilized perfluorohexane droplets.

9. The imaging reagent of claim 7, wherein the perfluorocarbon droplet is comprised of lipid-stabilized perfluorooctylbromide droplets.

10. A method for imaging a subject in vivo, comprising administering an effective amount of an imaging reagent of claim 1 and imaging the subject with $^{19}$F-MRI and/or positron emission tomography.

11. The method of claim 10, wherein the $^{19}$F-MRI and positron emission tomography are performed simultaneously.

12. The imaging reagent of claim 1, wherein a is an integer from 1 to 10.

13. The imaging reagent of claim 1, wherein b is an integer from 3 to 10.

14. The imaging reagent of claim 1, wherein the compound of the Formula I is $CF_3-(CF_2)_7-(CH_2)_3-^{18}F$.

* * * * *